United States Patent
Park

(10) Patent No.: US 9,852,509 B2
(45) Date of Patent: Dec. 26, 2017

(54) METHOD FOR TIBIA RESECTION ALIGNMENT APPROXIMATION IN KNEE REPLACEMENT PROCEDURES

(71) Applicant: Somersault Orthopedics Inc., Pleasanton, CA (US)

(72) Inventor: Ilwhan Park, Walnut Creek, CA (US)

( * ) Notice: Subject to any disclaimer, the term of this patent is extended or adjusted under 35 U.S.C. 154(b) by 0 days.

(21) Appl. No.: 14/531,337

(22) Filed: Nov. 3, 2014

(65) Prior Publication Data
US 2015/0125060 A1 May 7, 2015

Related U.S. Application Data

(63) Continuation-in-part of application No. 14/516,298, filed on Oct. 16, 2014.

(60) Provisional application No. 61/962,166, filed on Nov. 1, 2013, provisional application No. 61/962,333, filed on Nov. 4, 2013.

(51) Int. Cl.
| | |
|---|---|
| *G06K 9/00* | (2006.01) |
| *G06T 7/00* | (2017.01) |
| *A61B 17/15* | (2006.01) |
| *G06T 7/73* | (2017.01) |
| *A61B 5/055* | (2006.01) |
| *A61B 5/00* | (2006.01) |

(52) U.S. Cl.
CPC .......... *G06T 7/0097* (2013.01); *A61B 17/157* (2013.01); *G06T 7/0012* (2013.01); *G06T 7/73* (2017.01); *A61B 5/055* (2013.01); *A61B 5/4504* (2013.01); *G06T 2207/10088* (2013.01); *G06T 2207/10116* (2013.01); *G06T 2207/20101* (2013.01); *G06T 2207/30008* (2013.01)

(58) Field of Classification Search
None
See application file for complete search history.

(56) References Cited

U.S. PATENT DOCUMENTS

| | | | | |
|---|---|---|---|---|
| 4,736,737 A | * | 4/1988 | Fargie ................. | A61B 17/157 606/88 |
| 5,037,423 A | * | 8/1991 | Kenna ..................... | A61F 2/38 606/86 R |
| 8,617,171 B2 | * | 12/2013 | Park ....................... | B23P 17/04 606/87 |
| 8,617,175 B2 | * | 12/2013 | Park ..................... | A61B 17/155 606/89 |

(Continued)

*Primary Examiner* — Avinash Yentrapati
(74) *Attorney, Agent, or Firm* — Stephen E. Zweig

(57) ABSTRACT

Aspects of the present disclosure involve systems, methods, computer program products, and the like, for utilizing a series of images of a patient's anatomy to determine a cut plane for use during a knee procedure. To determine a cut plane for use during a knee replacement procedure, the 2D images may be analyzed by a computer program to determine a best fit plane through one or more points along the proximal surface of the tibia and to determine one or more features of depressions within the proximal surface. With these landmarks identified in the images, a cut plane through the tibia for use during a TKA procedure may be determined. Further, the location of these features in the images may be determined by analyzing the gray scale value of one or more pixels around a selected point on the image. The pixel with the lowest gray scale value may then be assumed to be the edge of the cortical bone in the 2D image.

24 Claims, 14 Drawing Sheets

(56) References Cited

U.S. PATENT DOCUMENTS

| | | | | |
|---|---|---|---|---|
| 8,715,291 B2* | 5/2014 | Park | ........................ | A61B 17/15 |
| | | | | 606/87 |
| 9,017,336 B2* | 4/2015 | Park | ...................... | A61B 17/155 |
| | | | | 606/88 |
| 9,208,263 B2* | 12/2015 | Pavlovskaia | ............ | A61B 19/50 |
| 2004/0143178 A1* | 7/2004 | Leitner | ............... | A61B 19/5244 |
| | | | | 600/407 |
| 2005/0010230 A1* | 1/2005 | Crofford | ............... | A61B 17/175 |
| | | | | 606/81 |
| 2009/0270868 A1* | 10/2009 | Park | ........................ | A61B 17/15 |
| | | | | 606/87 |
| 2010/0042105 A1* | 2/2010 | Park | ........................ | A61B 17/15 |
| | | | | 606/87 |
| 2011/0214279 A1* | 9/2011 | Park | ........................ | B23P 17/04 |
| | | | | 29/592 |
| 2011/0282473 A1* | 11/2011 | Pavlovskaia | ............ | A61B 19/50 |
| | | | | 700/98 |
| 2012/0265496 A1* | 10/2012 | Mahfouz | ................. | A61B 17/14 |
| | | | | 703/1 |
| 2013/0197687 A1* | 8/2013 | Pavlovskaia | ............ | A61B 19/50 |
| | | | | 700/118 |
| 2015/0081029 A1* | 3/2015 | Bojarski | .................. | A61F 2/389 |
| | | | | 623/20.32 |
| 2015/0125060 A1* | 5/2015 | Park | ........................ | A61B 19/50 |
| | | | | 382/131 |

* cited by examiner

METHOD FOR TIBIA RESECTION ALIGNMENT APPROXIMATION IN KNEE REPLACEMENT PROCEDURES

CROSS-REFERENCE TO RELATED APPLICATIONS

This application is a continuation-in-part and claims priority to U.S. patent application Ser. No. 14/516,298 entitled "METHOD FOR KNEE RESECTION ALIGNMENT APPROXIMATION IN KNEE REPLACEMENT PROCEDURES", naming Ilwhan Park as inventor and filed on Oct. 16, 2014, the entirety of which is hereby incorporated by reference herein. This application also claims priority under 35 U.S.C. §119(e) to U.S. Provisional Application No. 61/962,166 entitled "IMPROVEMENTS IN TIBIA ALIGNMENT FOR RESECTION", filed on Nov. 1, 2013 and U.S. Provisional Application No. 61/962,333 entitled "IMPROVEMENTS IN TIBIA ALIGNMENT FOR RESECTION", filed on Nov. 4, 2013, both of which are incorporated by reference in its entirety herein.

TECHNICAL FIELD

Aspects of the present disclosure generally relate to systems and methods for an accurate determination of relevant dimensions and alignments (lengths, angles, etc.) associated with a procedure for partial or total replacement of a knee component of a patient. Additional aspects of the present disclosure generally relate to systems and methods for identifying a cortical bone edge in a two-dimensional image of a knee component of a patient.

BACKGROUND

Through over-use, traumatic events and/or debilitating disease, a person's joint may become damaged to the point that the joint is repaired. One type of procedure to address damage to a person's joint is an arthroplasty procedure. Arthroplasty is a medical procedure where a joint of a patient is replaced, remodeled, or realigned. Damage to the joint may result in a reduction or wearing away of cartilage in the joint area, which operates to provide frictional, compressive, shear, and tensile cushioning within the joint. As such, reduction in cartilage in a joint causes pain and decreased mobility of the joint. To combat this joint pain, a patient may undergo the arthroplasty procedure to restore function and use of the damaged joint.

One type of arthroplasty procedure is known as Total Knee Arthroplasty (TKA). In general, TKA involves replacing the diseased or damaged portion of the knee with metal or plastic components that are shaped to approximate the replaced portion or shaped to allow movement of the joint and relieve the joint pain. Thus, a TKA procedure may include replacement of a portion of the femur and a portion of the tibia that make up the knee joint. Similar procedures may be performed on other damaged joints, such as a hip, a shoulder, an elbow, and the like. General discussion of arthroplasty procedures herein are directed specifically to TKA-type procedures, but may be applied to arthroplasty procedures of other types of joints.

In a TKA procedure, a damaged portion of the femur is cut off and replaced with a metal or plastic component that is shaped to mirror or approximate the replaced portion. The metal or plastic component may be impacted onto the femur or fixed using a type of surgical cement or other fastening system. Further, a damaged portion of the tibia may also be removed and replaced with a generally flat metal or plastic component that is shaped to mirror or approximate the replaced portion. The tibia replacement implant may also be attached to the tibia through impaction onto the bone or fixed using a type of cement. In essence, the damaged knee joint is replaced with a prosthetic knee. In general, the femur implant and the tibia implant are mated to form a prosthetic joint that approximates the shape and operation of the replaced knee joint. In some examples, a plastic surface is placed between the femur implant and the tibia implant to prevent metal-on-metal interaction between the implants during use of the replaced joint.

As mentioned above, a TKA procedure often involves the removal and replacement of portions of the femur and/or tibia of the injured knee. During the removal, the portions of the femur and tibia may be cut, drilled, resurfaced, and the like to create a surface on the bones that mates with the respective implants. In one particular example, the ends of the bones (distal end of the femur and proximal end of the tibia) may be completely removed to create generally flat surfaces to which the implants are mated. Once the mating surfaces for the implants are created on the receiving bones, the implants may then be attached to the bones as described above.

Although the broad outline of the TKA procedures is described above, there is much to consider when performing the procedure. For example, patients may undergo a preoperative planning phase including one or more consultations with a doctor a month or more before the TKA is performed. In addition, alignment of the implants in the joint with the rest of the patient's anatomy is crucial to the longevity of the implant and the implant's effectiveness in counteracting the pre-TKA joint condition. As such, systems and methods have been developed to produce customized arthroplasty cutting jigs that allow a surgeon to quickly and accurately perform the necessary resections of the bones that result in a successful TKA procedure. In particular, cutting jigs may be generally customized for the particular patient's joint undergoing the TKA procedure to ensure that the implants align with the patient's anatomy post-procedure. Through the use of such customized cutting jigs, the TKA procedure is both more accurate (ensuring more longevity to the implants) and quicker (reducing the time required for the surgical procedure, thereby reducing the potential for post-surgery complications).

In general, cutting guides or cutting jigs used in TKA procedures may attach to one or more bones of the knee and provide a cut line to the surgeon for use during the TKA surgery. In particular, a femur cutting jig may attach to the distal end of the femur and include a cut guide or line. A surgeon, during the procedure, inserts a saw device into or through the cut line to resect the distal end of the femur. Similarly, a tibia cutting jig may attach to the proximal end of the tibia and include a cut line that the surgeon uses to resect the proximal end of the tibia. In this manner, the ends of the femur and tibia are resected by the surgeon during the TKA procedure, thereby creating a smooth mating surface for the implants. As should be appreciated, the location and angle of the cut plane through the respective bone surface indicated by the cutting jig may determine the overall effectiveness of the TKA procedure. As such, a cutting jig utilized during the procedure should be designed to provide the proper location and orientation of the cut plane on the bones of the affected joint such that treatment of the region can be performed accurately, safely, and quickly.

Conventional jigs may be complicated to create, suffer from inaccuracies, overly time consuming to generate, overly expensive to generate, and many other concerns. Thus, while such systems may be useful, there are numerous opportunities to advance the art. It is with these and other issues in mind, among others, that various aspects of the present disclosure were developed.

SUMMARY

One implementation of the present disclosure may take the form of a method for determining a cut plane through a human tibia for an arthroplasty procedure on a human knee. The method may include the operations of receiving a plurality of two-dimensional (2D) images of a patient's joint subject to the arthroplasty procedure at a computing device, determining a best fit plane for a plurality of points along a table surface of a human tibia of a first set of 2D images of the plurality of 2D images, the table surface comprising at least a portion of the proximal end of the human tibia, and calculating a cut plane for use during the arthroplasty procedure on a human knee, wherein the cut plane is parallel to the calculated best fit plane for the plurality of points along the table surface of the human tibia of the first set of 2D images of the plurality of 2D images. In addition, the operations may further include generating a cutting jig for the arthroplasty procedure comprising a cut slot corresponding to the calculated cut plane.

Another implementation of the present disclosure may take the form of a system for processing a medical scan of a patient in preparation for an arthroplasty procedure on a human knee. The system may comprise a network interface configured to receive one or more medical images of a patient's anatomy and a processing device in communication with the network interface; and a computer-readable medium in communication with the processing device configured to store information and instructions. When the instructions are executed by the processing device, the system performs the operations of receiving a plurality of two-dimensional (2D) images of a patient's joint subject to the arthroplasty procedure at a computing device, determining a best fit plane for a plurality of points along a table surface of a human tibia of a first set of 2D images of the plurality of 2D images, the table surface comprising at least a portion of the proximal end of the human tibia, and calculating a cut plane for use during the arthroplasty procedure on a human knee, wherein the cut plane is parallel to the calculated best fit plane for the plurality of points along the table surface of the human tibia of the first set of 2D images of the plurality of 2D images. Additionally, the instructions may generate a cutting jig for the arthroplasty procedure comprising a cut slot corresponding to the calculated cut plane.

DETAILED DESCRIPTION

Figure 1:
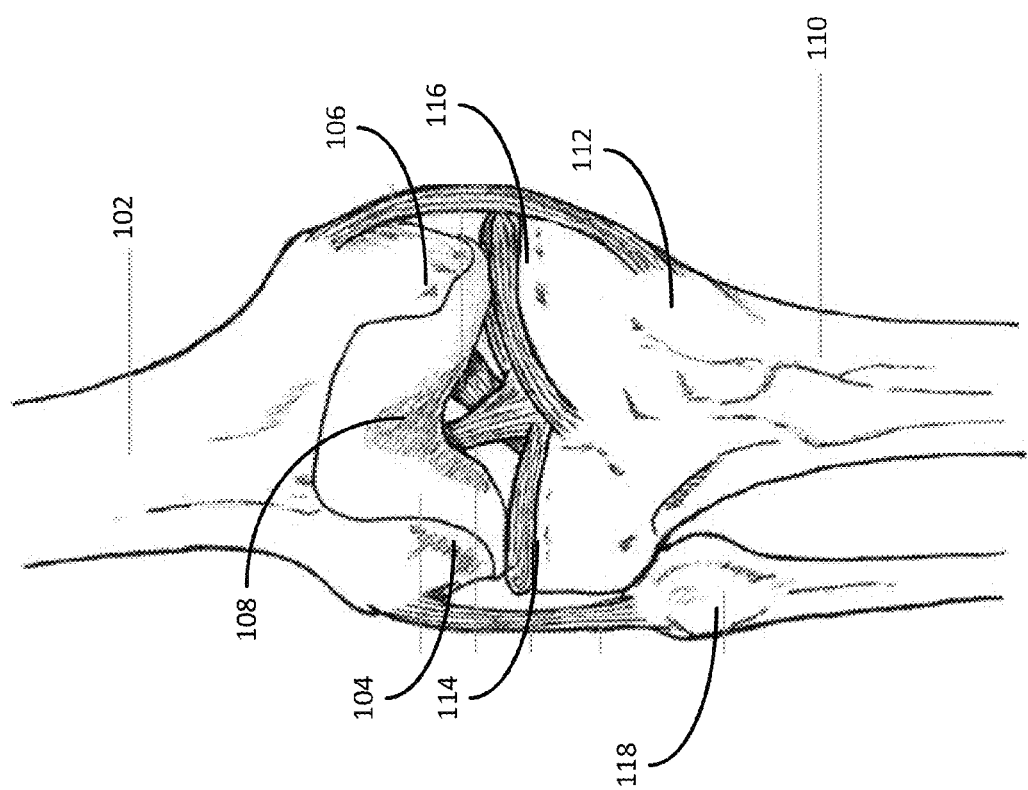
FIG. 1 is an anterior view of a knee joint illustrating the femur, tibia and ligaments of the joint.

Aspects of the present disclosure involve systems, methods, computer program products, manufacturing processes and the like, for utilizing a series of images of a patient's anatomy to determine a cut plane for use during a knee procedure, which may be used to create a tibia cutting jig useful in a partial or total knee replacement. In particular, the present disclosure provides for a method of utilizing one or more two-dimensional (2D) images of the patient's joint to undergo an arthroplasty procedure. The method includes receiving the 2D images of the joint from an imaging device and determining the location within at least one of the 2D images of the patient's cortical bone edge. Ultimately, the jig is fit to cortical bone (the hard outer bone surface) rather than other parts of the knee being replaced, such as soft tissue surrounding the knee and the like. In general, the location of the cortical bone edge of the patient's knee is determined by analyzing the gray scale value of one or more pixels around a selected point on the image. In particular, a range of pixels around the selected point provides a range of gray scale values that may be analyzed to determine the pixel with the lowest gray scale value. This pixel may then be assumed to be the edge of the cortical bone in the 2D image.

To determine a cut plane for use during a knee replacement procedure, the 2D images may be analyzed by a computer program or a user of a computing device to determine several landmarks or aspects of the patient's knee anatomy. In one particular example, one or more of the landmarks or aspects may be determined through the edge detection of the cortical bone described above. For example, one or more points along a proximal surface of the tibia in one or more images of the tibia may be found through the edge detection. With these points identified, the computing device may determine a best fit plane through or near the points. In addition, one or more features of depressions within the proximal surface of the tibia may also be identified to aid the computing device in determining the depth for the cut plane. Additional consideration may be made to the type of implant selected for the procedure in determining the depth of the cut plane. In general, the cut plane may be oriented parallel to the calculated best fit plane at the determined depth. Through the methods described herein, a reliable and sturdy cut plane for purposes of a knee implant may be determined. Further, the procedure to determine the cut plane through the tibia does not require the generation of a 3D model of the patient's knee so that the TKA procedure may occur more quickly and efficiently than conventional procedures.

To aid in the description below of the customized arthroplasty cutting jigs and methods for creating said jigs, a brief discussion of the bone anatomy of the human knee is now included. As mentioned above, the present disclosure may be applied to any type of joint of a patient. However, for ease of understanding, the discussion herein is limited to particulars of the human knee as an example of the joint relating to the present disclosure procedure and apparatus.

FIG. 1 illustrates an anterior view of a patient knee joint, and in particular, the femur 102, tibia 110, and ligaments of the knee. The femur 102 includes two eminences, known as the condyles 104,106. Between the condyles is a smooth depression called the trochlea 108 or trochlear groove. The condyles are divided into a medial condyle 104 and a lateral condyle 106. The tibia 110 includes a head with two tuberosities, a medial tuberosity 114 and a lateral tuberosity 116. The medial 114 and lateral tuberosity 116 generally form concave surfaces (known as the tibia plateau) in the head 112 of the tibia 110. In general, the condyles 104,106 form two convex surfaces that engage and articulate over the two convex surfaces of the tuberosities 114,116 of the tibia 110 during movement of the knee joint. A fibula bone 118 is also shown in FIG. 1 that attaches to the tibia 110 at or near the tibia head 112. Additional features and details of the femur 102 and the tibia 110 of the knee joint are discussed in more detail below with reference to FIGS. 2 through 5.

Figure 2A:
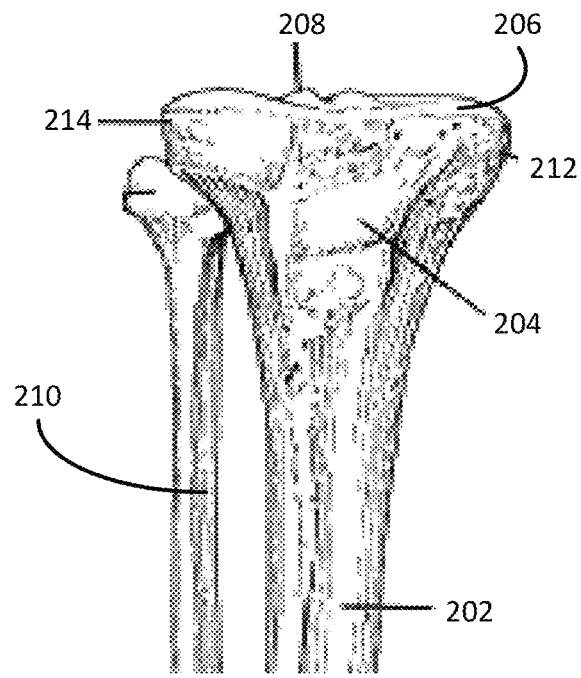
FIG. 2A is an anterior view of an upper tibia.
Figure 2B:
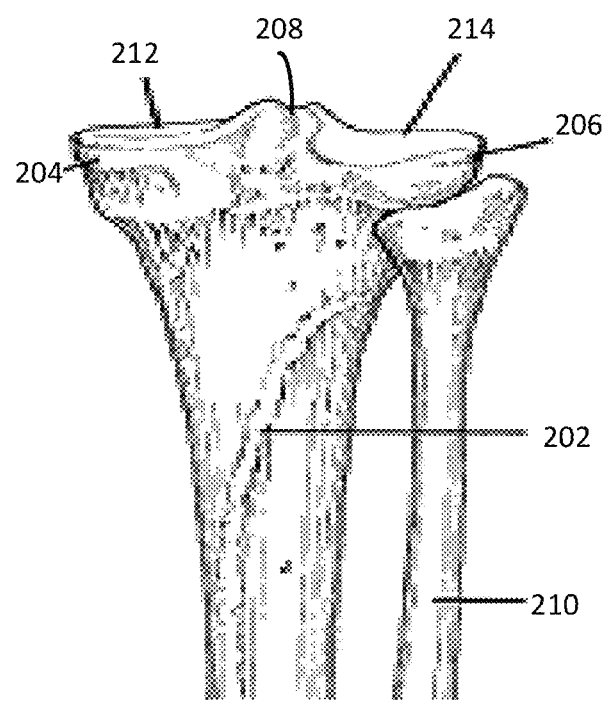
FIG. 2B is a posterior view of an upper tibia.

FIG. 2A is an anterior view of the upper or proximal tibia and FIG. 2B is a posterior view of the upper tibia. The proximal end of the tibia generally includes a tibia shaft 202 and a tibia head 204. The tibia head 204 forms a plateau surface 206 at the proximal end of the tibia. The plateau surface 206 includes a spine feature 208 that runs down the middle of the plateau surface between the anterior and posterior (front and back) of the knee. Attached to the tibia head 204 is the fibula 210. The tibia head 204 also includes a lateral condyle depression 212 and a medial condyle depression 214 that correspond to and articulate with the condyles of the femur to form the knee joint.

Figure 3:
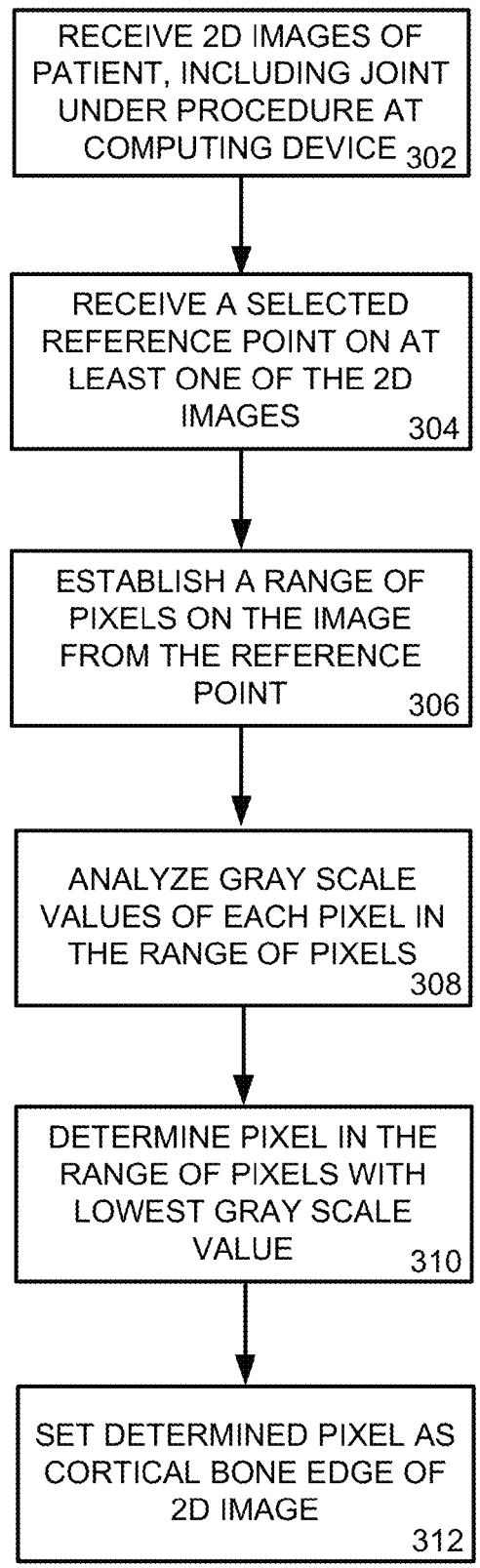
FIG. 3 is a flowchart illustrating a method for locating a cortical bone edge in a two-dimensional (2D) image of a patient's tibia.

In general, during a TKA procedure, portions of the proximal end of the tibia (such as that shown in FIGS. 2A and 2B) and the distal end of the femur are removed by the surgeon and replaced with respective implants that approximate the shape and function of the ends of the respective bones. To aid in resecting portions of the femur and tibia, the surgeon may employ a femur cutting jig and tibia cutting jig that provides a cut or resection line for the surgeon to cut along. The cut plane provided by the cutting jig may be determined based on one or more landmarks or features of a patient's anatomy, such as the edge of the tibia bone, illustrated in an image of the patient's joint. Thus, it may be beneficial for determining the cut plane for the TKA procedure to accurately identify the cortical bone, or outer shell, of the patient's tibia and/or femur from one or more image slices of the patient's knee. One method for locating a cortical bone edge in a 2D image of a patient's bone is described in the flowchart of FIG. 3. Although more or fewer operations may be included in the process of detecting the cortical bone of the tibia, the operations of FIG. 3 provide an example of one such process that utilizes 2D images of the patient's joint. Further, although described herein in relation to detecting a cortical bone edge of a patient's femur, similar operations may be performed to locate the bone edge of a patient's tibia in the images or any other bone surface of the patient in the images.

Figure 4:
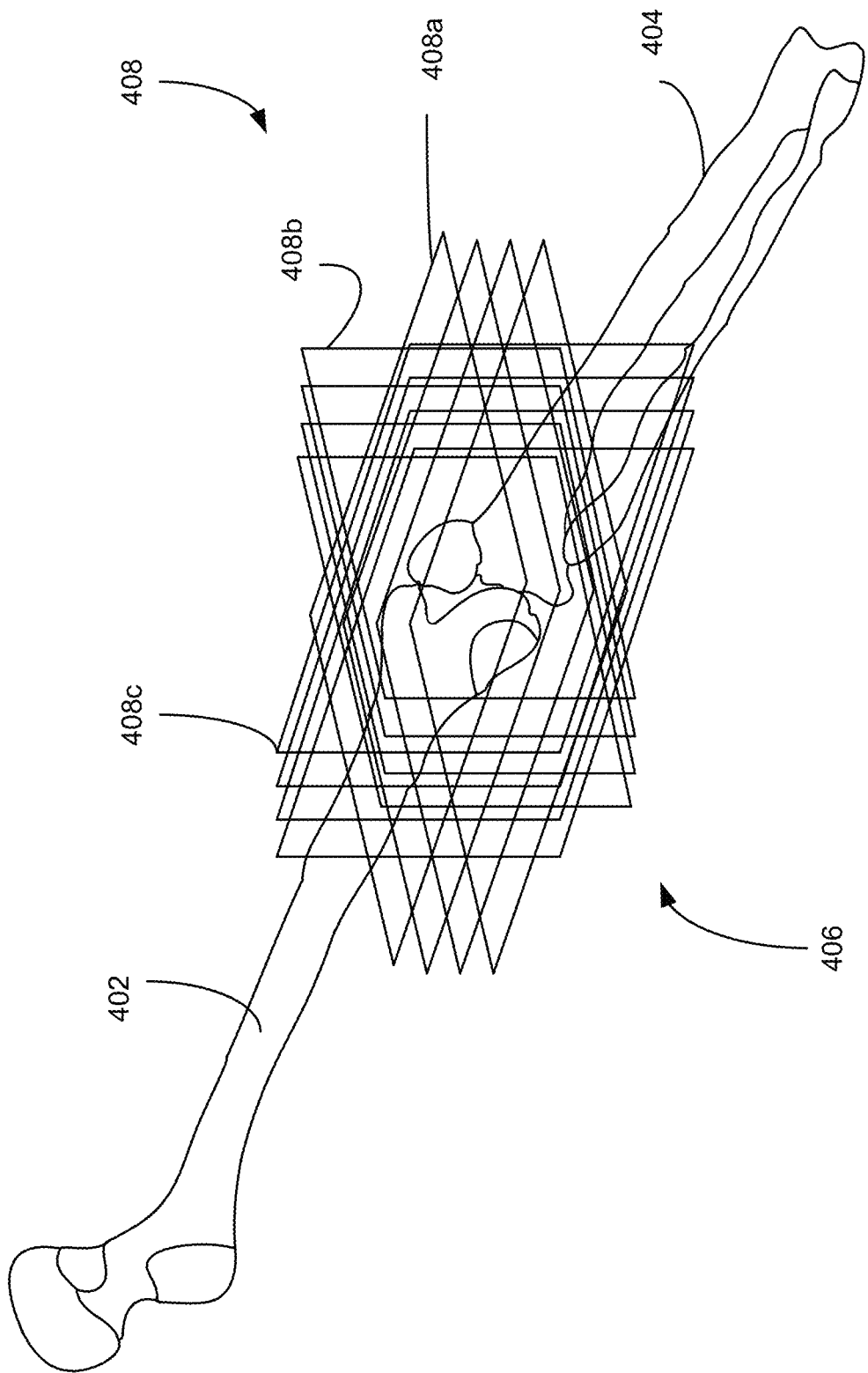
FIG. 4 is an illustration of one embodiment for obtaining 2D images of a knee of a patient.

Beginning in operation 302, a series of two-dimensional (2D) images of the patient's joint on which the arthroplasty procedure is to be performed may be obtained. The 2D images of the patient's joint may be obtained from an imaging device (such as an X-ray or magnetic resonance imaging (MRI) machine) from several aspects of the joint. For example, FIG. 4 illustrates one embodiment for obtaining 2D images of a knee 406 of a patient. In particular, the patient's knee 406, including portions of the femur 402 and tibia 404, is scanned in a MRI knee coil to generate a plurality of 2D knee coil MRI images (image slices) of the patient's knee. In one embodiment, the 2D images 408 of the knee include a plurality of image slices taken along a coronal plane 408a through the knee, a plurality of image slices taken along an axial plane 408b through the knee, and/or a plurality of image slices taken along a sagittal plane 408c through the knee. In other embodiments, the 2D images may be any combination of coronal, sagittal and/or axial views. In one embodiment, the MRI imaging spacing for the 2D knee coil images may range from approximately 2 mm to approximately 6 mm and may vary from aspect to aspect. For example, the coronal image slices 408a may be spaced 2 mm apart, while the axial image slices 408b may be spaced 6 mm apart.

While the embodiments herein are discussed in the context of the imaging being via an MRI machine, in other embodiments the imaging is via computed tomography (CT), X-ray, or other medical imaging methods and systems. Further, although it is discussed herein as a scan of the knee, the 2D images may be obtained for any joint or other area of the patient's body, such as images of the patient's ankle, hip, shoulder, etc.

Figure 5:
FIG. 5 is a screenshot of a magnetic resonance imaging (MRI) image of a patient's femur.

Once the 2D images of the joint at issue are obtained, the images may be received at or otherwise provided to a computing device for processing. The computing device may receive the images through any form of electronic communication with the imaging device. In one particular example, the 2D images may be obtained by the imaging device (such as the MRI imaging machine) and transmitted to a website (and associated data storage) accessible by the computing device. In general, however, the 2D images may be obtained from the imaging machine in any fashion for further processing by the computing device. One example of such an MRI image of a patient's knee is illustrated in the screenshot of FIG. 5. In particular, the MRI image 500 is a coronal image slice of a patient's knee roughly along a plane through the middle of the knee illustrating the femur 502 and the tibia 504 of the knee joint. Although the MRI image 500 of FIG. 5 is referred to for the discussion herein, it should be appreciated that any type of coronal, sagittal, or axial image may be utilized.

In operation 304, the computing device may receive a selected reference point in at least one of the 2D images. To provide the reference point in one embodiment, an operator of the computing device may sit at a monitor or other interface of the computing device through which the images are viewed. Utilizing a software program executed by the computing device, the operator may view the 2D images and provide the one or more reference markers on at least one of the 2D images. These electronic markers may correspond to one or more reference points within the images for use by the computing device to determine a cortical bone portion of the bone illustrated in the 2D image. The operations to utilize the reference points to determine the bone edge or the cortical bone in the image are described in more detail below.

In another embodiment, a program executed by the computing device may obtain the 2D images and determine the one or more reference points within the images, with or without the aid of an operator of the computing device. For example, the computing device may analyze the 2D images and determine a first reference point within the image corresponding to near a presumed cortical bone surface of the bones in the image. In yet another embodiment, one or more of the operations of the method of FIG. 3 are performed by the operator, while other operations are performed by the computer program. For example, a program executed by the computing device may instruct a user of the device to locate a reference point in a particular area of the image by requesting the user to indicate the reference point near what the user may presume to be the cortical bone edge in the image. In another example, the program may analyze the 2D image to locate a potential area in the image that may include the cortical bone of the image and instruct the user to select a reference point within the potential area near a perceived cortical bone feature. As such, any of the operations and methods described herein may be performed by an operator of the computing device or the computing device itself through hardware, software, or a combination of both hardware and software.

Figure 6:
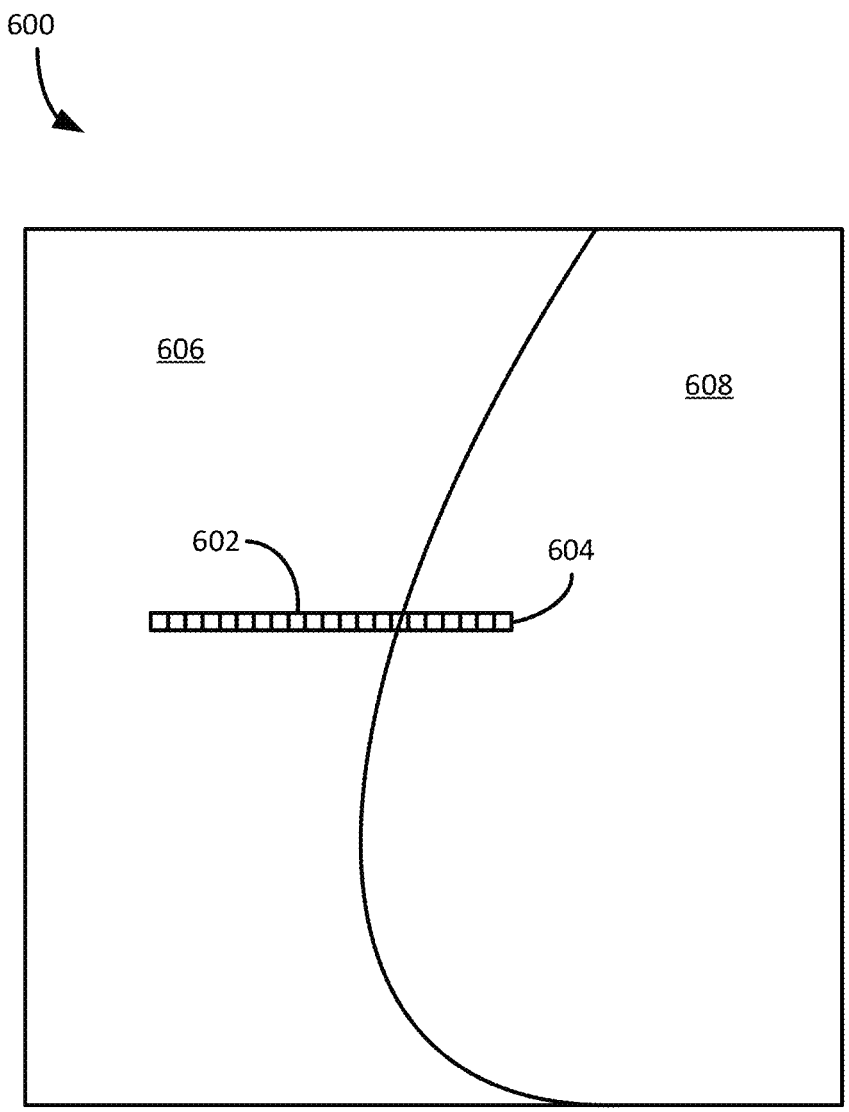
FIG. 6 is a representative screenshot of a close-up view of an MRI image of a patient's femur with a selected point and a horizontal pixel range around the selected point.

FIG. 6 is a screenshot of a close-up view of an MRI image of a patient's femur with a selected point 602 and a horizontal pixel range 604 around the selected point. The image 600 illustrates a non-bone region 606 and a bone region 608 of the patient. For example, the image 600 may represent a small portion of the MRI image 500 shown in FIG. 5 of the patient's knee joint. The image 600 of FIG. 6 illustrates a portion of that image that includes a region 606 illustrating portions of the patient's knee that does not include the image of the femur and a region 608 illustrating portions of the patient's knee that includes the image of femur bone. In one embodiment, the transition from the non-bone region 606 to the bone region 608 indicates the edge of the patient's femur, or the cortical bone of the patient's femur in the image 600.

Also shown in the image 600 of FIG. 6 is the reference point 602. As mentioned above, the reference point 602 may be indicated in the image by the user through operation of the computing device. Thus, the user may analyze the image and select a point on the image at or near the cortical bone of the femur. In another embodiment, the computing device may analyze the image and select a point that is at or near the cortical bone feature of the femur in the image. The reference point 602 may be located in the image 600 in the non-bone region 606 or in the bone region 608. Regardless of the embodiment utilized, it should be appreciated that it is not required that the reference point be at the cortical bone edge in the image 600. Rather, the reference point may be in any position within the image, as discussed in more detail below. However, it may be preferable for the reference point 602 to be located in the image 600 near the cortical bone edge. By placing the reference point 602 near the bone edge in the image 600 ensures that the pixel range 604 captures the bone edge within the pixel range.

Returning to the flowchart of FIG. 3, in operation 306 the computing device may establish a range of pixels 604 in the 2D image around the reference point 602. In the embodiment illustrated in FIG. 6, the range of pixels 604 includes pixels along the same horizontal axis of the reference point 602. In particular, the computing device associates the selected reference point 602 to a particular pixel of the image, referred to herein as the reference pixel. In the embodiment shown, the pixel range 604 is the pixels of the image on either side of the reference pixel 602 in the same horizontal axis of the image as the reference pixel. For example, the pixel range 604 may include the adjacent ten pixels to the left of the reference pixel and the adjacent ten pixels to the right of the reference pixel. That is, the pixel range 602 includes a horizontal row of pixels of the image 600 of twenty-one pixels (the reference pixel, ten pixels to the left of the reference pixel, and ten pixels to the right of the reference pixel). The particular row of the image of the range of pixels 602 is determined from the selected reference point or reference pixel 602 in the image.

As should be appreciated, the embodiment illustrated in the image 600 is but one example of the range of pixels 604 utilized by the computing device. In another embodiment, the range of pixels may be a vertical range of pixels that extend up and down the image from the reference pixel 602. An example of a vertical range of pixels is discussed in more detail below with reference to FIG. 8. In another embodiment, the range of pixels 604 may include a combination of pixels within the same row and same column as the reference pixel 602. In yet another embodiment, the range of pixels 604 may include pixels not in the same row and/or same column as the reference pixel 602, or a combination of pixels in the same row and/or the same column as the reference pixel and pixels not in the same row and/or same column. Further, the range of pixels 604 may not be adjacent to each other within the range such that spaces between the pixels of the range may be present. Also, the range of pixels 604 may include any number of pixels. For example, it is not required that the range of pixels 604 illustrated in FIG. 6 include 21 pixels. Rather, the range 604 may include any number of pixels in the same row of the image as the reference pixel 602. As also discussed in more detail below, the number of pixels in the range of pixels 604 may be selected to increase the likelihood that the cortical bone edge in the image is located within the range. In general, the range of pixels 604 around the selected reference pixel 602 may include any number of pixels in any relation to the reference pixel.

Figure 7:
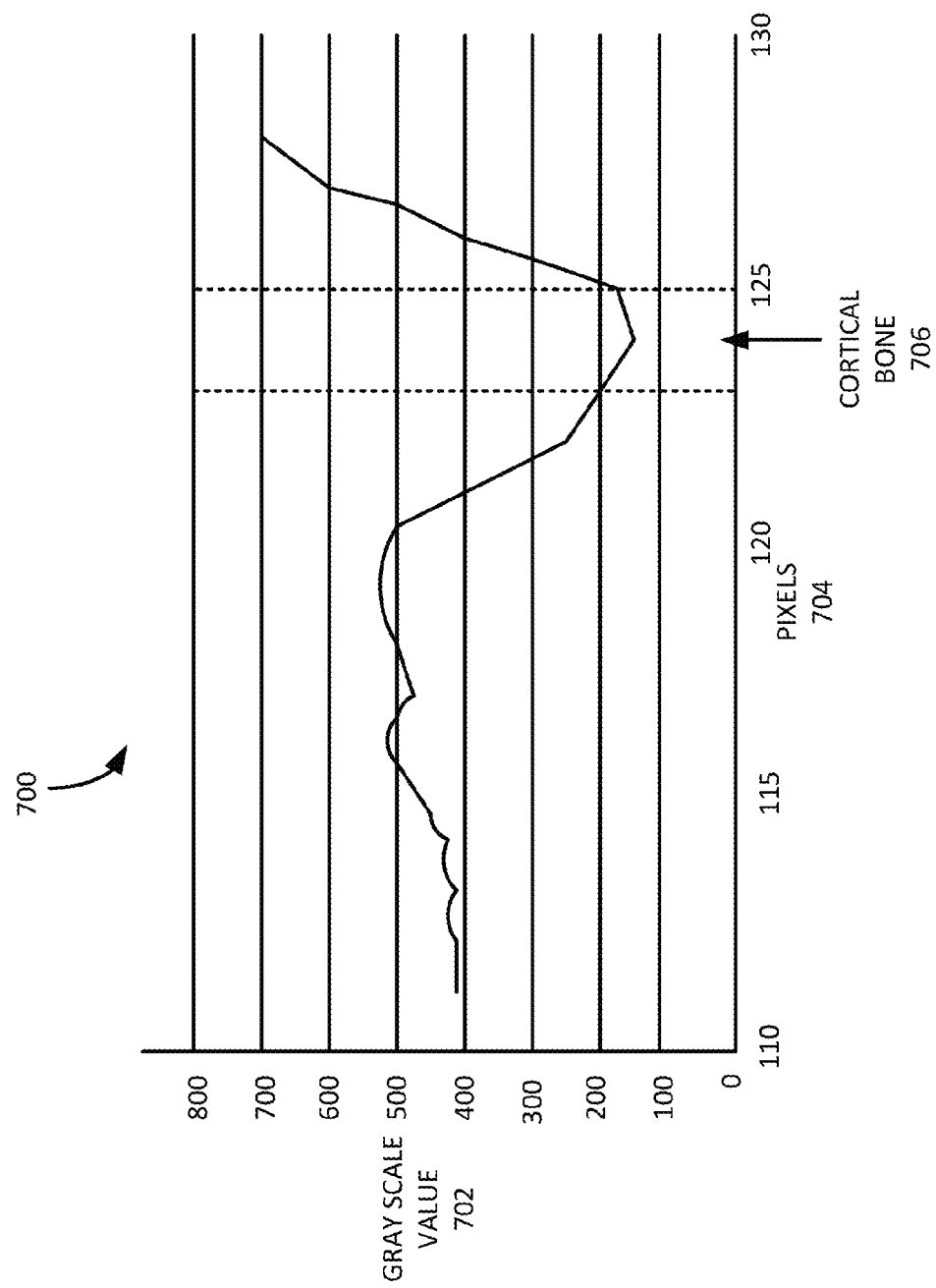
FIG. 7 is a chart illustrating gray scale values of the pixels in the pixel range of the MRI image of FIG. 6.

With the range of pixels 604 for analysis established, the computing device may analyze the gray scale value associated with one or more of the pixels in the range of pixels. FIG. 7 is a chart illustrating the gray scale values of the pixels in the pixel range 604 of the MRI image 600 of FIG. 6. Although shown in FIG. 7 as a chart of the gray scale values of the pixels in the pixel range, it should be appreciated that such a chart may not be created by the computing device. Rather, the computing device may simply analyze the gray scale values associated with one or more of the pixels in the pixel range 604 and determine the lowest value of gray scale in the range. However, for simplification of the discussion herein, reference is made to the chart of FIG. 7.

The chart 700 includes an x-axis of gray scale values of the pixels in the image and a y-axis of a reference number assigned to the pixels in the pixel range 604. In the example shown, the pixels of the pixel range are assigned a reference number from 110 to 130. The reference numbers assigned to the pixels may be associated with the placement of the pixels within the pixel range 604. For example, pixel number 110 may be the leftmost pixel in the pixel range and pixel number 130 may be the rightmost pixel. The reference number provided to each pixel in the pixel range 604 may correspond to a reference number used by the computing device for that particular pixel in the image 600. Thus, pixel number 110 may be the $110^{th}$ pixel in that particular row of the image 600. A similar convention may be used for a vertical pixel range such that the lowest reference number may be assigned to lowest pixel in the vertical pixel range and the highest reference number may be assigned to highest pixel in the vertical pixel range. In general, any type of reference number may be used to index the pixels in the pixel range 604. In one particular example, the pixels in the image are assigned a pixel number by the computing device that is universal to the image and the reference number in the chart may be associated or the same as the pixel number assigned by the computing device.

As shown in the chart 700, the gray scale values 702 for each of the pixels 704 in the pixel range 604 are graphed. In operation 310 of the flowchart of FIG. 3, the computing device may analyze the gray scale values 702 of the pixels 704 in the pixel range to locate the pixel or pixels with the lowest gray scale value. In the graph 700, the lowest gray scale value 706 occurs at or about pixel 124. Once the pixel with the lowest gray scale value is determined by the computing device, the computing device may then associate the location of the pixel with the lowest gray scale value in the range of pixels as the cortical bone edge of the image in operation 312. In general, the transition in the image from a darker region to a lighter region may indicate the cortical bone edge in the image. Thus, the location of the pixel in the pixel range 604 with the lowest gray scale value indicates the cortical bone edge in the accompanying image.

In another embodiment, the computing device may be configured to not only identify the pixel with the lowest gray scale value, but may also verify that the gray scale values along the pixel range provide a valley shape to the graph. The valley shape provides a stronger indication that the cortical bone edge is located at the lowest point within the valley as the gray scale values transition from a dark region to a light region and back to a dark region along the pixel range. Such a valley suggests the cortical bone edge in the image resides in the valley portion of the gray scale value chart 700. In particular, as the x coordinate (704) increases in the graph 700, the gray scale intensity of pixels within the range of pixels tends to decrease to a lowest number, corresponding to a highest bone density, then increase beyond that point. Further, in some embodiments the computing device may indicate more than one pixel in the range as being associated with the cortical bone edge in the image. In this embodiment, a group of pixels may be designated as providing the cortical bone edge such that the computing device may assume the cortical bone edge in the image resides somewhere within the group of pixels. One such group of pixels in which the cortical bone edge lies in shown in chart 700 as pixels 123-125.

As mentioned above, the computing device may analyze the pixels of the range of pixels to determine the pixel with the lowest gray scale value. In one embodiment, the computing device may calculate the lowest gray scale value of the range of pixels where the pixel intensity can be approximately expressed as:

$$I(x, y_m) = p0m + p1m\ x + p2m\ x^2 + p3m\ x^3 + p4m\ x^4,$$
$$(x = n = n0, m0+1, \ldots)$$

where the row index x assumes values x=1, 2, 3, . . . and the coefficients p0m, p1m, p2m, p3m, and p4m can be found by inversion of a 3×3 or 4×4 matrix involving powers of the pixel index numbers, n=n0, n0+1, n0+2, n0+3, n0+4. The $4^{th}$ degree of polynomial $I(x, y_m)$ in the equation may be less than 4 in appropriate circumstances. An approximation for a location of the "center" of the cortical bone can be estimated by a solution x=(x(min; m) (n0≤x(min)≤n0+4) of the equation $$dI(x, y_m)/dx = p1m + 2p2m\ x + 3p3m\ x^2 + 4p4m\ x^3 = 0.$$

Figure 8:
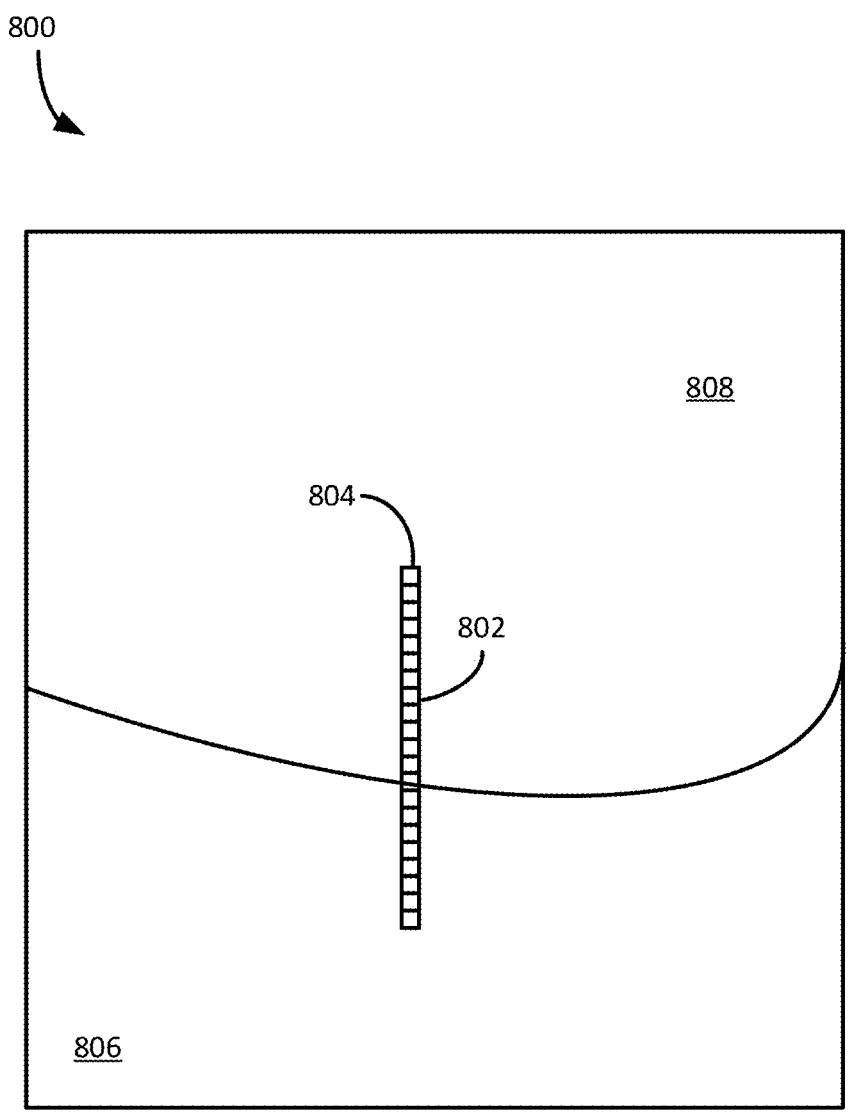
FIG. 8 is a screenshot of the MRI image of the patient's femur with a selected point and a vertical pixel range around the selected point.

The method for determining the cortical bone edge in the image of the patient's femur may also be utilized for other types of pixel ranges. As mentioned above, the pixel range may be a vertical range, or a number of pixels in the same column as the reference pixel. FIG. 8 is a screenshot of the MRI image 800 of the patient's femur with a selected point 802 and a vertical pixel range 804 around the selected point. Similar to the screenshot discussed above with reference to FIG. 6, the image 800 may include a reference point 802 associated with a reference pixel of the image. A range of pixels 804 may also be oriented around the reference pixel. However, in this example, the range of pixels 804 forms a vertical column of pixels around the reference pixel. The orientation of the range of pixels 804 is just one example of the orientation of the range of pixels associated with the reference point.

In one embodiment, the orientation of the range of pixels may be known by the computing device when requesting the location of the reference point from the user of the computing device. For example, the computing device may request the user place the reference point in the image near a particular cortical edge of the bone of the image, such as the outer edge of the medial condyle of the femur in the image. Based on this request, the computing device may then create a horizontally-oriented range of pixels around the selected reference point to capture the cortical bone edge of the femur in the image. Similarly, the computing device may request the user place the reference point in the image near the most distal point of the femur in the image. Based on this request, the computing device may then create a vertically-oriented range of pixels around the selected reference point to capture the cortical bone edge of the femur in the image. In this manner, the computing device may request the placement of the reference point near a particular edge of the femur in the image and apply a range of pixels accordingly. In yet another embodiment, the computing device may analyze the image, select a particular reference point corresponding to a particular edge of the femur, and apply a particular orientation of a range of pixels around the reference point to attempt to capture the cortical bone edge of the femur in the image.

Figure 9:
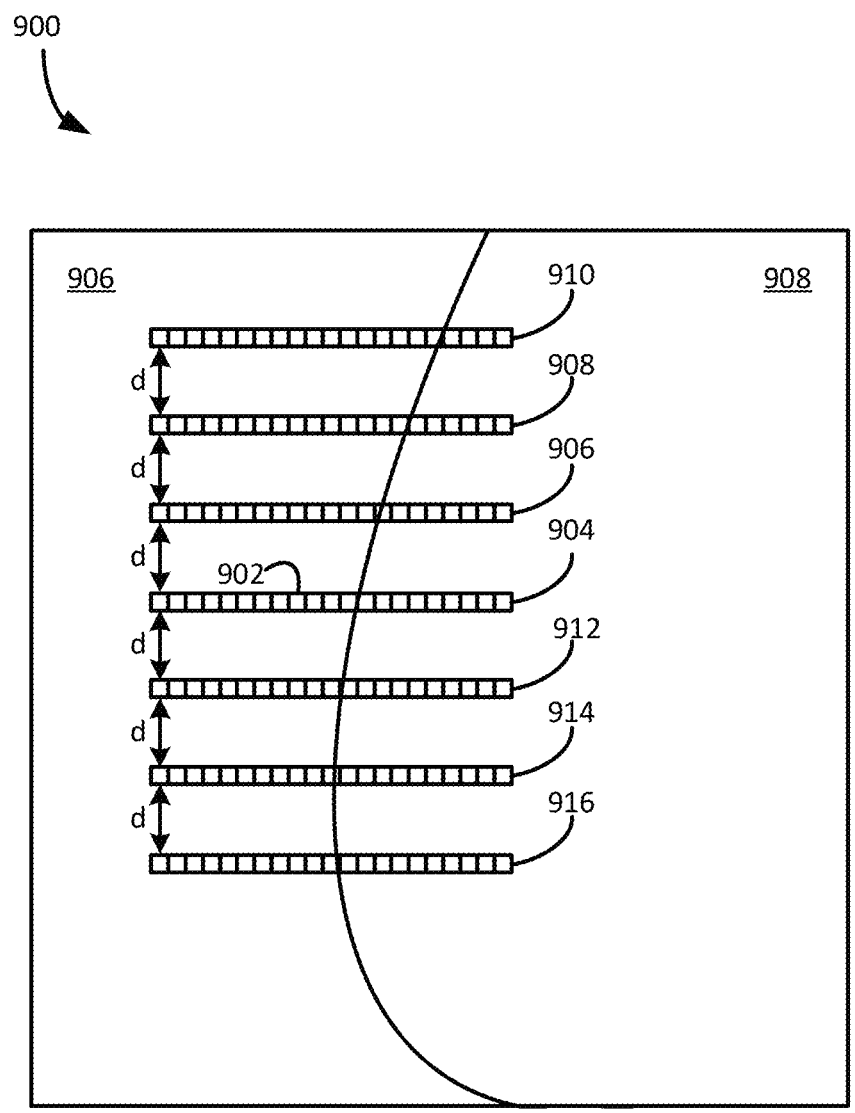
FIG. 9 is a screenshot of the MRI image of the patient's femur with a plurality of horizontal pixel ranges extending from a selected point by a set distance value.

In addition, the computing device may also be configured to analyze several ranges of pixels in relation to determining the edge of the bone in an image based on a reference point in the image. For example, FIG. 9 is a screenshot of the MRI image of the patient's femur with a plurality of horizontal pixel ranges extending from a selected point by a set distance value. The image 900 is similar to the images described above with relation to FIG. 6 and FIG. 8. Also similar to the above description, the computing device may receive a reference point 902 from a user of the computer device or from an analysis of the image 900 by the computing device. A first range of pixels 904 may be created around the reference pixel 902 as described above and analyzed to determine a lowest gray scale value within the range of pixels. However, in addition to locating the pixel with the lowest gray scale value in the first range of pixels, the computing device may create additional ranges of pixels to further locate the cortical bone edge in the image.

In particular, the computing device may be configured to create additional ranges of pixels 906-916 in relation to the first range of pixels 904. For example, a second range of pixels 906 may be oriented a distance "d" from the first range of pixels in any direction. In the particular example illustrated in FIG. 9, the second range of pixels 906 is set off from the first range of pixels 904 vertically by the distance. As such, the second range of pixels 906 is oriented in a separate row of the image 900 from the first range of pixels 904. Upon the placement of the second range of pixels 906 in the image 900, the computing device may analyze the gray scale values of the pixels in the second range of pixels to determine the pixel or group of pixels with the lowest gray scale value. The edge of the cortical bone in the second range of pixels 906 may then be associated with the pixel with the lowest gray scale value. A third range of pixels 908 may then be created and placed in the image the distance d from the second range of pixels 906. The pixels of the third range of pixels 908 may be analyzed to determine the lowest gray scale value and the cortical bone edge within the third range of pixels.

In this manner, multiple ranges of pixels 904-916 may be created and analyzed to detect the edge of the cortical bone in the image 900. Further, the ranges of pixels 904-916 may be offset from each other by the distance d in any direction. For example, ranges of pixels 906-910 are oriented in rows above the reference point 902, while ranges of pixels 912-916 are oriented in ranges in rows below the reference point, with the distance between each range of pixels being the value d. Also, the placement of the ranges of pixels 904-916 may be in any direction from the reference pixel 902. Thus, ranges of pixels 904-916 may be horizontal or vertical from the first range of pixels 904. In addition, the ranges of pixels 904-916 may be in any orientation, such as vertical, horizontal, blocks, diagonal, etc. and may include more or fewer pixels than the first range of pixels 904. Finally, the distance between the ranges of pixels 904-916 may be any distance and may vary between the various ranges of pixels in the image 900. In this manner, the computing device may utilize pixel ranges 904-916 to locate the edge of the cortical bone in many locations within the image 900.

In one particular embodiment, the placement of the ranges of the pixels 904-916 may be adjusted upon the detection of the cortical bone edge in previous ranges of pixels. For example, upon the analysis of the second range of pixels 906 and the third range of pixels 908 in the image 900, the computing device may determine that the cortical bone is moving to the right within the ranges of pixels as the ranges of pixels are placed closer to the top of the image. In such a scenario, the computing device may begin orienting additional ranges of pixels to the right from the previous range of pixels. In this manner, the placement of the ranges of pixels may be adjusted as the cortical bone edge is determined through the analysis of previous ranges of pixels. In a similar manner, the orientation of the ranges of pixels may also be adjusted as the edge of the cortical bone is determined. In general, any configurable aspect of the range of pixels may be adjusted during the method described as more information about the location of the cortical bone edge is determined within the image.

Through the operations described above, a computing device may automatically determine or approximate the cortical bone or edge of the femur or tibia of a 2D image of a patient's knee joint. The location of the bone edge may aid a user of the computing device or the computing device itself in determining a cut plane for use in a TKA procedure of the patient's knee. For example, from the 2D images of the patient's knee and, in particular, one or more landmarks of the patient's knee identified in the 2D images, a cut plane through the patient's femur and tibia may be determined for use during a knee replacement procedure. The one or more landmarks may coincide with one or more edges of the patient's bone in the images. Thus, determining one or more edges of the patient's bone in the 2D images through the method described above may provide the one or more landmarks within the images to determine the cut plane used during the resection portion of the TKA. Because the method described above is more accurate and/or quicker than the user manually identifying the edge of the bone edge in the images through a computing device interface, the use of the method may provide a more accurate cut plane for use during the knee replacement procedure.

One example of the use of the edge detection of the patient's bone in one or more 2D images of the patient's joint is now described. In particular, a cut plane to resect a portion of a tibia for use during a partial or total knee replacement procedure is provided. In general, the cut plane is determined from one or more landmarks or other portions of the patient's tibia. Such landmarks may be identified in one or more image slices of the patient's knee and applied to the cut plane orientation. In one particular embodiment, the cut plane may be imported into a customized cutting jig for use during the TKA procedure. In general, during a TKA procedure, portions of the proximal end of the tibia (such as that shown in FIGS. 2A and 2B) are removed by the surgeon and replaced with an implant that approximates the shape and function of the ends of the respective bones. To aid in resecting portions of the tibia, the surgeon may employ a tibia cutting jig that provides a cut or resection line for the surgeon to cut along.

To determine the cut plane, the computing device may receive the 2D images or image slices of the joint from an imaging device and create a customized jig template from the images. Once the template for the cutting jig is created by the computing device utilizing one or more of the landmarks on the 2D images, a cutting or milling program is generated by the computing device. The cutting or milling program may then be provided to a milling machine to create the cutting jig corresponding to the milling program. The cutting jig is thus customized to the landmarks identified in the series of 2D images of the patient's joint. Further, the procedure does not require the generation of a three-dimensional (3D) model of the patient's anatomy to create the customized nature of the cutting jig. Rather, by utilizing one or more mating shapes that contact the joint anatomy at particular contact points of the joint anatomy corresponding to the identified landmarks in the 2D images, the customization of the cutting jig is achieved. Further, because the procedure does not require the generation of a 3D model, the customized cutting jigs may be produced more quickly and efficiently than previous customization methods.

Figure 10:
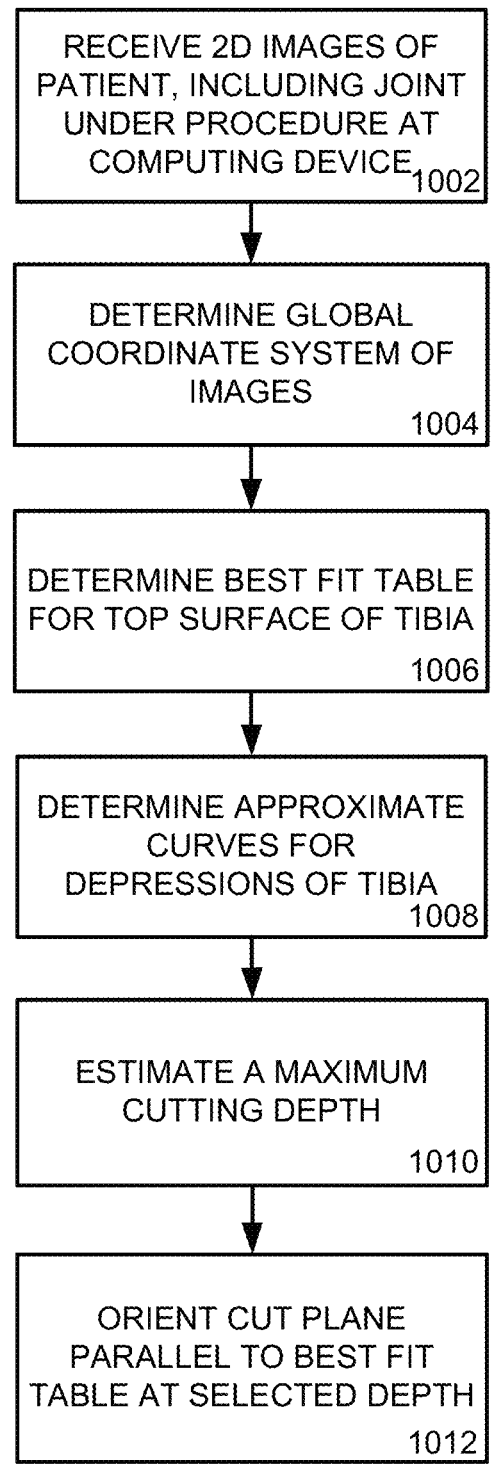
FIG. 10 is a flowchart illustrating a method for determining a cut plane of a tibia for use during a knee replacement procedure from one or more 2D images of the knee.

FIG. 10 is a flowchart illustrating a method for determining a cut plane of a tibia for use during a knee replacement procedure from one or more 2D images of the knee. The operations of the method of FIG. 10 may be performed by a computing device in operation by a user of the computing device. In addition, one or more of the operations may be performed by the computing device utilizing the cortical bone edge detection method discussed above. In general, the method provides an indication of a potential cut plane for use during a knee replacement procedure. Such a cut plane may be translated into a cutting jig for use during the procedure.

Beginning in operation 1002, a series of two-dimensional (2D) images of the patient's joint on which the arthroplasty procedure is to be performed may be obtained. The 2D images of the patient's joint may be obtained from an imaging device (such as an X-ray or magnetic resonance imaging (MRI) machine) from several aspects of the joint. Once the 2D images of the joint at issue are obtained, the images may be entered into a computing device for processing. The computing device may receive the images through any form of electronic communication with the imaging device. In one particular example, the 2D images may be obtained by the imaging device (such as the MRI imaging machine) and transmitted to a website accessible by the computing device. In general, however, the 2D images may be obtained from the imaging machine in any fashion for further processing by the computing device.

In operation 1004, the 2D images of the joint are processed to determine a global coordinate system for the images and/or to identify one or more points or landmarks associated with the patient's joint for establishing the cut plane. In general, a global coordinate system of the patient's joint in the images corresponds to the natural alignment of the patient prior to damage to the joint. For example, the global coordinate system of the images may correspond to an axial plane through the center of the patient's knee that is parallel to the ground while the patient is walking. It should be appreciated, however, that reformatting the 2D images to achieve an image that is in anatomical alignment of the knee is not required. Rather, the reformatting of the images may approximate images of anatomical alignment of the knee for the global coordinate system.

Figure 11:
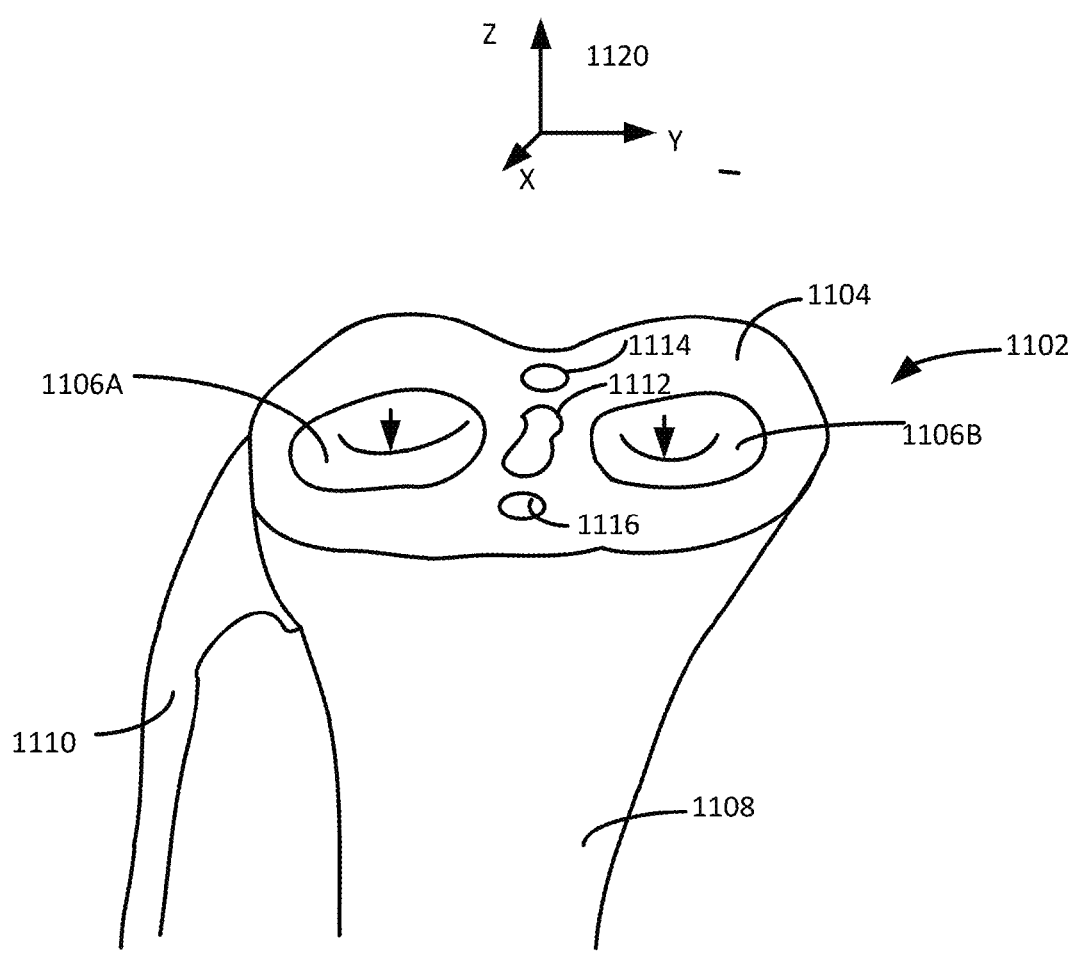
FIG. 11 is an illustration of a perspective view of an upper portion of a tibia of a patient.

FIG. 11 is a perspective illustration of an upper portion of a tibia of a patient. Portions of the tibia 1102 model may be illustrated in the one or more image slices of the patient's tibia mentioned above. That is, the tibia 1102 may be a collection of the image slices of the patient's tibia such that portions of the tibia of FIG. 11 correspond to portions of the patient's tibia, as provided in the received 2D images. In particular, the tibia 1102 includes a tibia shaft 1108 and a fibula 1110. A table surface 1104 is located on the proximal end of the tibia 1102. This surface includes two spaced apart surface depression regions, 1106A and 1106B, a spine aperture 1112, a posterior cruciate ligament (PCL) aperture 1114 and an anterior cruciate ligament (ACL) aperture 1116. The table surface 1104 and depressions may be used to determine a cut plane for a resection of the tibia during a TKA procedure, as explained in more detail below.

Also included in FIG. 11 is a global coordinate axis 1120. In general, the global coordinate system 1120 includes an x-axis, y-axis, and a z-axis. In one particular embodiment, the z-axis coincides with, or is approximately parallel to, a direction of a line segment that extends between a low end of the tibia shaft to a high end of the tibia shaft, or a tibia shaft axis 1108. As such, the computing device may determine the tibia shaft axis directly from the images, or an approximation of the tibia shaft axis may be provided to the computing device, such as from a user of the device. In one specific example, the user may provide a shaft reference line in one or more of the images that approximates the tibia shaft axis. Also, the y-axis of the global coordinate system 1120 may extend in a direction (such as in the sagittal view) corresponding to a coronal view of the knee, and the x-axis is perpendicular to the y-axis and the z-axis.

In one particular embodiment, one or more of the 2D images may be reformatted along the global coordinate system. For example, the reformatting of the images may include reorientation of the images and/or extrapolation of data from between image slices to align or approximate the global coordinate system. Thus, each of the 2D images in the set of images may be reformatted to account for the angle of the images obtained during imaging. In one embodiment, one or more reference lines or points within the images may be analyzed when reorienting or reformatting the images along the global coordinate system. Such reference points or reference lines may be obtained through the operations described above to locate the edge of the femur bone in the images provided to the computing device. In yet another embodiment, the global coordinate system may be determined by the computing device in relation to the image or images with no additional formatting of the images occurring.

In operation 1006, a computing device determines a best fit plane or best fit table for a plurality of points located along the table surface 1104 of the tibia 1102. In particular, multiple points along the table surface 1104 of the tibia 1102 are identified by the computing device. Such points generally do not include points or surfaces within the depressions of the table surface 1104. Thus, points within the two spaced apart surface depression regions, 1106A and 1106B, the spine aperture 1112, the PCL aperture 1114 and the ACL aperture 1116 are not included in the points used to determine the best fit plane. In one embodiment, the locations along the table surface 1104 are provided to the computing device by a user of the device. In another embodiment, the computing device may utilize the operations described above in relation to the cortical bone location to determine the edge of the cortical bone in one or more images of the patient's knee that correspond to the table surface 1104. For example, the computing device may analyze a first coronal image slice of the knee and, utilizing the methods described above, determine one or more points along the table surface 1104 of the tibia 1102 for that particular slice. The identified points in the image slice may then be used as one point that determines the best fit plane as described in more detail below. Additional coronal view image slices may similarly be analyzed to determine the points along the table surface 1104 of the tibia 1102.

As mentioned, the points on the table surface 1104 of the tibia 1102 may be determined through the operations described above to locate the bone edge. In particular, utilizing an image slice of the patient's tibia, the computing device may place or receive a reference point near the table surface 1104 in the image. The computing device may then utilize the operations above to locate the table surface 1104 edge. This point, along with other points identified in other image slices of the tibia 1102 may be used to determine a best fit plane through the multiple points. In particular, the points identified in the image slice(s) may lie various positions in the three dimensional space of the global coordinate. The best fit plane thus provides a reference plane that best fits the points in three dimensional space. This best fit plane may be used as a reference plane for determining a cut plane for use during a TKA procedure of the patient's knee.

Figure 12:
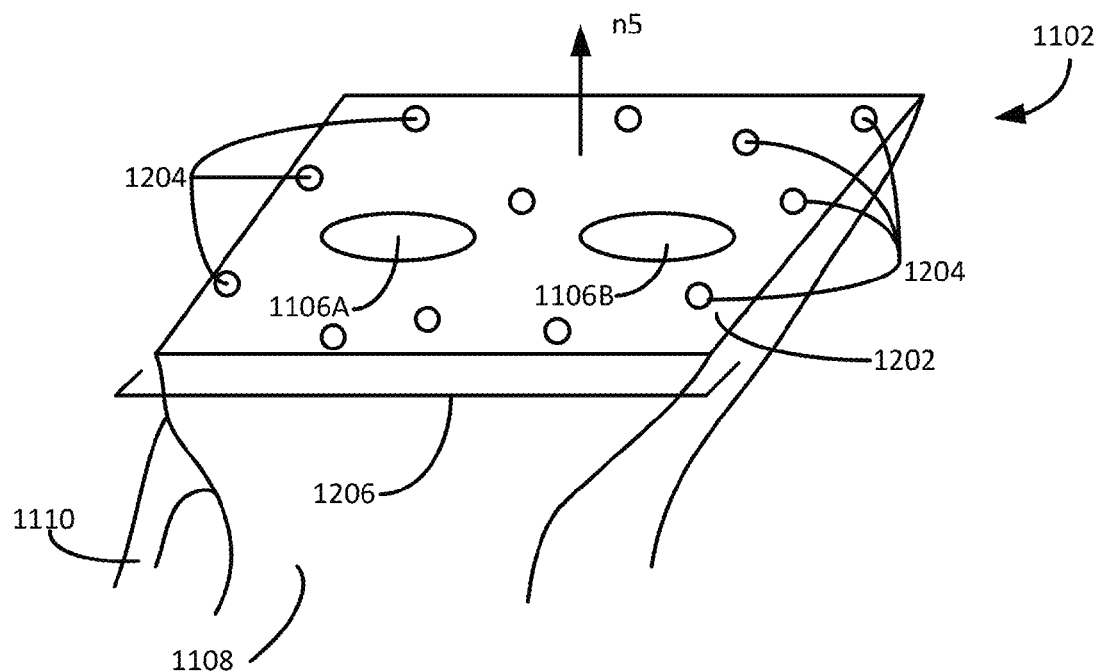
FIG. 12 is an illustration of a perspective view of a tibia table defined by a best fit table through a plurality of points on the tibia proximal end.

One method to determine the best fit plane corresponding to the table surface 1104 of the tibia 1102 in the 2D images is now presented. In particular, FIG. 12 is an illustration of a perspective view of a best fit table imposed on a tibia table through a plurality of points on the tibia proximal end. Thus, although not illustrated in FIG. 12, features of the tibia table would still be present on the tibia image. For example, the tibia spine discussed above would lie above the best fit table 1202. The tibia 1102 of FIG. 12 is the same tibia illustrated in FIG. 11 and includes similar reference numbers. Thus, the tibia 1102 includes a tibia shaft 1108, a fibula 1110, and two spaced apart surface depression regions, 1106A and 1106B. However, the tibia 1102 of FIG. 12 also illustrates a best fit plane 1202 corresponding to multiple points indicated on the table surface of the tibia. The points 1204 indicated on the tibia 1102 of FIG. 12 may correspond to the points located above in the image slices of the patient's tibia.

As should be appreciated, the best fit plane 1202 may not pass through every point 1204 indicated on the table surface. Rather, in some instances, the best fit plane 1202 may pass adjacent to or otherwise near one or more of the points. In general, the best fit plane 1202 defines a plane shape that best fits the three dimensional location of each point on the table surface 1104, with some point lying above or below the generated plane.

One particular method to determine the best fit plane from the images is now presented. In particular, the best fit plane may be determined through a least squares plane calculation. Working with coordinates $(x_m, y_m, z_m)$ (m=1, 2, 3, ..., M) for locations 1204 on the table surface 1104, not including locations within the surface depression regions 1106A-B, the PCL aperture 1114, ACL aperture 1116 or the spine aperture 1112, parameters (ax,ay,az,p) for a Best Fit Table 1202 for the actual table surface 1104 are estimated, using an error function:

$$\varepsilon = \left\{ \sum_{m=1}^{M} x_m \alpha x + y_m \alpha y + z_m \alpha z - p \right\}^2 + \lambda(1 - \alpha x^2 - \alpha y^2 - \alpha z^2)$$

for which a constraint, $\alpha x^2 + \alpha y^2 + \alpha z^2 = 1$, is imposed on the direction cosines, through use of an undetermined multiplier $\lambda$. The parameter p represents a perpendicular distance from the coordinate origin to the Best Fit Table 1202.

Figure 13A:
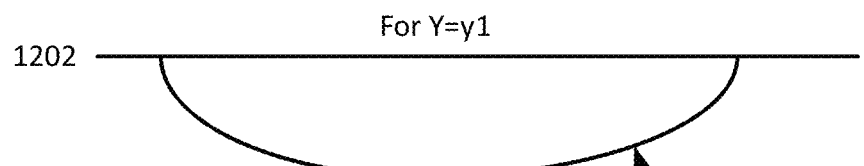
FIGS. 13A-C illustrate a sequence of curves representing depressions in the proximal end of the tibia of patient as illustrated in the images of the patient's knee.
Figure 13B:
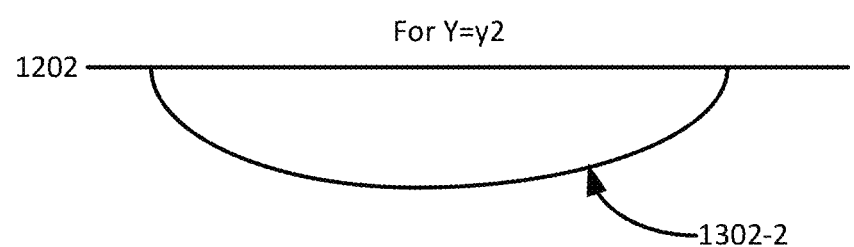
Figure 13C:
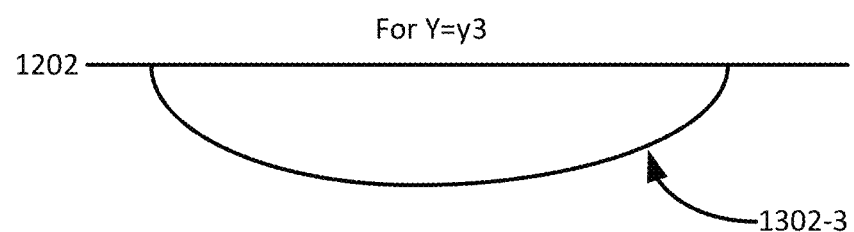

In addition to the best fit table, the computing device may also determine the shape of one or more depression curves on the tibia table to aid in the location of the cutting plane. In particular, the computing device determines approximate curves for each depression area on the table surface 1104 in operation 1008. More particularly, the computing device approximates a curve on the tibia table surface 1104 that passes through or adjacent to a location of maximum depth for the depression, relative to the best fit plane defined above. FIGS. 13A-C illustrate a sequence of curves representing depressions in the proximal end of the tibia of patient as illustrated in the images of the patient's knee. In particular, the curved line 1302-1 of FIG. 13A may represent the portion of the tibia corresponding to a depression of the tibia surface as illustrated in one of the images of the patient's tibia. This curve 1302-1 may be in the image slice located at a first y value along the y-axis of the global coordinate system. Similarly, the curved line 1302-2 of FIG. 13B may represent the portion of the tibia corresponding to a depression of the tibia surface as illustrated in one of the images of the patient's tibia located at another y value along the y-axis. Thus, through the various 2D images of the patient's tibia, several curves representing or approximating the depression curves on the tibia table surface 1104 may be created by the computing device. Similar to above, these curves may be obtained through the edge detection techniques described above. For example, the computing device may analyze a first sagittal image slice of the knee and, utilizing the methods described above, determine a curved line that represents the depression shape for that particular slice. Additional sagittal view image slices may similarly be analyzed to create the curved line that represents that portion of the depression in the images. In this manner, the curved lines (1302-1 through 1302-3) of FIGS. 13A-C of the tibia may be determined for additional analysis. Further, similar curved lines may be created for each of the depressions of the tibia surface 1104 as desired for calculation and determination of the cut plane.

Figure 14:
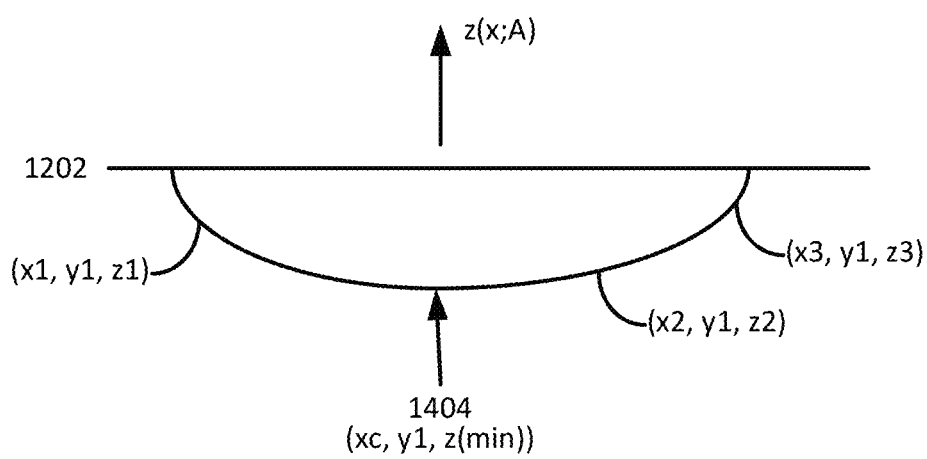
FIG. 14 illustrates a normal to one of the curves of FIGS. 13A-C utilized to determine a cut plane through the tibia.

The curve 1302-1 representing a depression of the tibia surface of a particular image slice is reproduced in FIG. 14. In general, the selected curve 1402 of FIG. 14 is the curve from the plurality of curves defining a depression of the tibia surface that has the largest depth. For example, for depression 1106A of the tibia surface 1104, the computing device determines the image slice illustrating the deepest point in the depression in the set of images representing the depression. In one example, the selected curve 1402 corresponds to the curve 1302-1 of the depression illustrated in FIG. 13A. A similar selected curve may be obtained for depression 1106B of the tibia. The following calculations may thus be performed by the computing device on selected curve illustrating the lowest depth for both depressions 1106A-B of the tibia surface 1104.

In particular, each of two, three or more sets of coordinates (xq,yq,zq) is determined for an intersection of a plane containing a unit length vector n5=(nx, ny, nz) shown in FIG. 12 that is normal to the Best Fit Table plane 1202 with each of the surface depression regions, 1106A and 1106B. Each of these intersections is approximated by a polynomial in x, such as a quadratic or cubic curve, $z(x) = z0 + z1\ x + z2\ x^2 + z3\ x^3$, relative to the Best Fit Table plane 1202, with a corresponding normal vector n5. A curve 1402 with the largest magnitude depth, $|z(x=x0)| = z(max)$ for each of the depression regions 1106A and 1106B, respectively, is selected. A curvature parameter κ1 is estimated for each selected curve at the corresponding maximum depth location, x=x0. A sector of a circle or oval, expressed as $(x-x0)^2 + z^2 = a^2$, that is the tangent to the curve 1402 at the maximum depth location 1404 is estimated for each of the depression regions 1106A and 1106B with curvature κ2=1/a. The curvatures, κ2 for depression 1106A and κ2 for depression 1106B, may be, but need not be, the same.

With the maximum depth of the depressions 1106A and 1106B determined, the computing device may calculate or estimate a maximum cutting depth for the cut plane in operation 1010. An example of a cut plane is illustrated in FIG. 12 as plane 1206. In one particular embodiment, the cut plane 1206 may be located below the maximum depth of one or more of the depressions 1106A and 1106B of the tibia surface. Thus, the computing device may utilize the calculated maximum depth of one or more of the depressions 1106A and 1106B of the tibia in the global coordinate system to determine a cutting depth of the cut plane 1206. This maximum cutting depth may be measured parallel from the best fit table 1202 determined above. Additionally, a surgeon may further determine an appropriate distance from the best fit table 1202 for positioning of the tibia cut plane 1206 along the z-axis of the tibia in the global coordinate system based on the implant intended for the particular patient.

In operation 1012, the cut plane 1206 for use in resecting the patient's tibia during a TKA procedure is determined. In particular, the cut plane 1206 may include a normal vector that is parallel to the normal vector of the best fit plane (n5) determined above. In this manner, the cut plane 1206 is parallel to the best fit plane of the tibia. A normal vector of the cut plane 1206 may be, in some embodiments, oriented in any direction that is approximately the same as the n5 direction, with a corresponding redefinition in the z-axis.

Through the operations described above, the orientation of the cut plane 1206 may be determined from the 2D images provided to the computing device. In this manner, various landmarks of the patient's tibia illustrated in the 2D images of the patient's knee may be utilized to determine an orientation of a cut plane to be used during a TKA procedure. Such a cut plane may be determined without the need to model the patient's knee or otherwise create a 3D interpretation of the images. As such, through the operations described above, a cut plane for use in TKA procedure is determined from the plurality of 2D images of the patient's joint.

Figure 15:
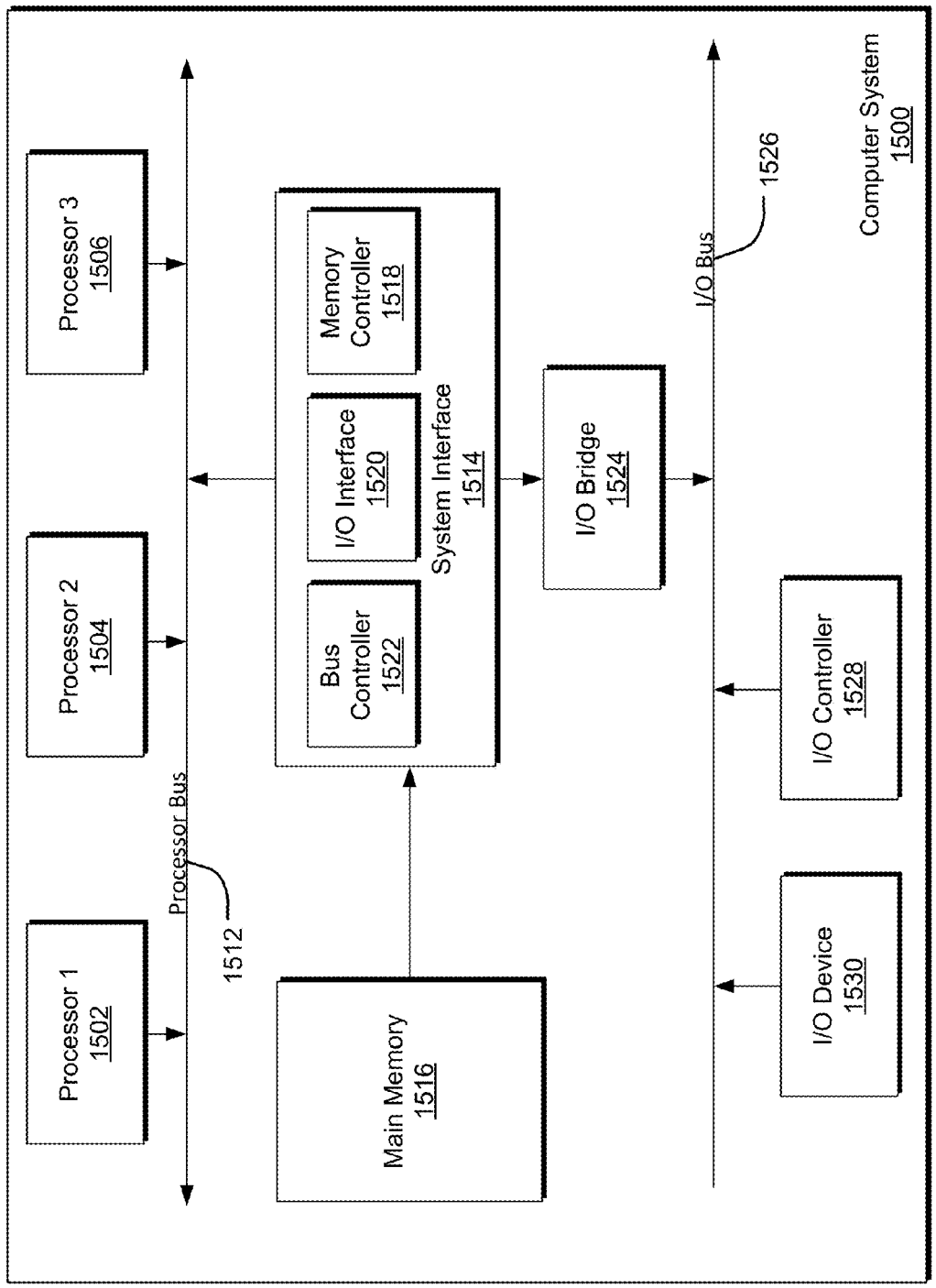
FIG. 15 is a block diagram illustrating an example of a computing device or computer system which may be used in implementing the embodiments disclosed above.

FIG. 15 is a block diagram illustrating an example of a computing device or computer system 1500 which may be used in implementing the embodiments disclosed above. The computer system (system) includes one or more processors 1502-1506. Processors 1502-1506 may include one or more internal levels of cache (not shown) and a bus controller or bus interface unit to direct interaction with the processor bus 1512. Processor bus 1512, also known as the host bus or the front side bus, may be used to couple the processors 1502-1506 with the system interface 1514. System interface 1514 may be connected to the processor bus 1512 to interface other components of the system 1500 with the processor bus 1512. For example, system interface 1514 may include a memory controller 1518 for interfacing a main memory 1516 with the processor bus 1512. The main memory 1516 typically includes one or more memory cards and a control circuit (not shown). System interface 1514 may also include an input/output (I/O) interface 1520 to interface one or more I/O bridges or I/O devices with the processor bus 1512. One or more I/O controllers and/or I/O devices may be connected with the I/O bus 1526, such as I/O controller 1528 and I/O device 1530, as illustrated.

I/O device 1530 may also include an input device (not shown), such as an alphanumeric input device, including alphanumeric and other keys for communicating information and/or command selections to the processors 1502-1506. Another type of user input device includes cursor control, such as a mouse, a trackball, or cursor direction keys for communicating direction information and command selections to the processors 1502-1506 and for controlling cursor movement on the display device.

System 1500 may include a dynamic storage device, referred to as main memory 1516, or a random access memory (RAM) or other computer-readable devices coupled to the processor bus 1512 for storing information and instructions to be executed by the processors 1502-1506. Main memory 1516 also may be used for storing temporary variables or other intermediate information during execution of instructions by the processors 1502-1506. System 1500 may include a read only memory (ROM) and/or other static storage device coupled to the processor bus 1512 for storing static information and instructions for the processors 1502-1506. The system set forth in FIG. 15 is but one possible example of a computer system that may employ or be configured in accordance with aspects of the present disclosure.

According to one embodiment, the above techniques may be performed by computer system 1500 in response to processor 1504 executing one or more sequences of one or more instructions contained in main memory 1516. These instructions may be read into main memory 1516 from another machine-readable medium, such as a storage device. Execution of the sequences of instructions contained in main memory 1516 may cause processors 1502-1506 to perform the process steps described herein. In alternative embodiments, circuitry may be used in place of or in combination with the software instructions. Thus, embodiments of the present disclosure may include both hardware and software components.

A machine readable medium includes any mechanism for storing or transmitting information in a form (e.g., software, processing application) readable by a machine (e.g., a computer). Such media may take the form of, but is not limited to, non-volatile media and volatile media. Non-volatile media includes optical or magnetic disks. Volatile media includes dynamic memory, such as main memory 1516. Common forms of machine-readable medium may include, but is not limited to, magnetic storage medium; optical storage medium (e.g., CD-ROM); magneto-optical storage medium; read only memory (ROM); random access memory (RAM); erasable programmable memory (e.g., EPROM and EEPROM); flash memory; or other types of medium suitable for storing electronic instructions.

It should be noted that the flowcharts above are illustrative only. Alternative embodiments of the present invention may add operations, omit operations, or change the order of operations without affecting the spirit and scope of the present invention. The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

I claim:

1. A method for determining a cut plane through a human tibia for an arthroplasty procedure on a human knee, the method comprising:

receiving a plurality of two-dimensional (2D) images of a patient's joint subject to the arthroplasty procedure at a computing device;

determining a plane for a plurality of points along a table surface of a human tibia of a first set of 2D images of the plurality of 2D images, the table surface comprising at least a portion of a proximal end of the human tibia, said plurality of points comprising at least three points;

wherein the plane for the plurality of points along the table surface of the human tibia is a best fit plane along the table surface of the human tibia within the at least one of the plurality of 2D images;

wherein the plurality of points along the table surface of the human tibia of the first set of 2D images are determined by:

obtaining a reference point on the at least one of the plurality of 2D images;

creating a range of pixels of the at least one of the plurality of 2D images from the reference point, wherein each pixel in the range of pixels comprises a gray scale value; and determining the pixel in a first range of pixels with the lowest gray scale value;

calculating a cut plane for use during the arthroplasty procedure on a human knee, wherein the cut plane is parallel to the calculated plane for the plurality of points along the table surface of the human tibia of the first set of 2D images of the plurality of 2D images; and generating a cutting jig for the arthroplasty procedure comprising a cut slot corresponding to the calculated cut plane.

2. The method of claim 1 wherein the best fit plane is calculated through a least squares plane calculation.

3. The method of claim 1 further comprising determining a cut plane depth on the human tibia, the cut plane depth comprising a distance measured distally along the human tibia from the best fit plane.

4. The method of claim 3 further comprising calculating a depression curve within at least one of the plurality of 2D images representing a depression feature of the table surface of the human tibia.

5. The method of claim 4 further comprising determining a maximum depth of the depression feature of the table surface of the human tibia from the depression curve.

6. The method of claim 5 wherein the cut plane depth is greater than the maximum depth of the depression feature of the table surface of the human tibia as measured from the best fit plane for the plurality of points along the table surface of the human tibia.

7. The method of claim 1 wherein calculating the cut plane for use during the arthroplasty procedure comprises: calculating a best fit plane normal vector to the best fit plane for the plurality of points along the table surface of the human tibia of the first set of 2D images of the plurality of 2D images; and orienting a normal vector of the cut plane to be parallel to the best fit plane normal vector.

8. The method of claim 1 wherein the calculated cut plane corresponds to a resection plane of the human tibia during a total knee arthroplasty procedure.

9. The method of claim 1 wherein the plurality of 2D images of a patient's joint subject to the arthroplasty procedure are magnetic resonance imagining (MRI) images.

10. A system for processing a medical scan of a patient in preparation for an arthroplasty procedure on a human knee, the system comprising:
a network interface configured to receive one or more medical images of a patient's anatomy; and a processing device in communication with the network interface; and
a computer-readable medium in communication with the processing device configured to store information and instructions that, when executed by the processing device, performs the operations of:
receiving a plurality of two-dimensional (2D) images of a patient's joint subject to the arthroplasty procedure at a computing device;
determining a plane for a plurality of points along a table surface of a human tibia of a first set of 2D images of the plurality of 2D images, the table surface comprising at least a portion of a proximal end of the human tibia said plurality of points comprising at least three points;
wherein the plane for the plurality of points along the table surface of the human tibia is a best fit plane along the table surface of the human tibia within the at least one of the plurality of 2D images;
wherein the plurality of points along the table surface of the human tibia of the first set of 2D images are determined by:
obtaining a reference point on the at least one of the plurality of 2D images;
creating a range of pixels of the at least one of the plurality of 2D images from the reference point, wherein each pixel in the range of pixels comprises a gray scale value; and
determining the pixel in a first range of pixels with the lowest gray scale value;
calculating a cut plane for use during the arthroplasty procedure on a human knee, wherein the cut plane is parallel to the calculated plane for the plurality of points along the table surface of the human tibia of the first set of 2D images of the plurality of 2D images; and
generating a cutting jig for the arthroplasty procedure comprising a cut slot corresponding to the calculated cut plane.

11. The system of claim 10 wherein the best fit plane is calculated through a least squares plane calculation.

12. The system of claim 10 wherein the information and instructions, when executed by the processing device, further performs the operation of determining a cut plane depth on the human tibia, the cut plane depth comprising a distance measured distally along the tibia from the best fit plane.

13. The system of claim 12 wherein the information and instructions, when executed by the processing device, further performs the operation of calculating a depression curve within at least one of the plurality of 2D images representing a depression feature of the table surface of the human tibia.

14. The system of claim 13 wherein the information and instructions, when executed by the processing device, further performs the operation of determining a maximum depth of the depression feature of the table surface of the human tibia from the depression curve.

15. The system of claim 14 wherein the cut plane depth is greater than the maximum depth of the depression feature of the table surface of the human tibia as measured from the best fit plane for the plurality of points along the table surface of the human tibia.

16. The system of claim 10 wherein calculating the cut plane for use during the arthroplasty procedure comprises:
calculating a best fit plane normal vector to the best fit plane for the plurality of points along the table surface of the human tibia of the first set of 2D images of the plurality of 2D images; and
orienting a normal vector of the cut plane to be parallel to the best fit plane normal vector.

17. The system of claim 10 wherein the calculated cut plane corresponds to a resection plane of the human tibia during a total knee arthroplasty procedure.

18. The system of claim 10 wherein the plurality of 2D images of a patient's joint subject to the arthroplasty procedure are magnetic resonance imagining (MRI) images.

19. A method for determining a cut plane through a human tibia for an arthroplasty procedure on a human knee, the method comprising:
receiving a plurality of two-dimensional (2D) images of a patient's joint subject to the arthroplasty procedure at a computing device;
determining a plane for a plurality of points along a table surface of a human tibia of a first set of 2D images of the plurality of 2D images, the table surface comprising at least a portion of a proximal end of the human tibia;
calculating a depression curve within at least one of the plurality of 2D images representing a depression feature of the table surface of the human tibia;
calculating a cut plane for use during the arthroplasty procedure on a human knee, wherein the cut plane is parallel to the calculated plane for the plurality of points along the table surface of the human tibia of the first set of 2D images of the plurality of 2D images;

determining a cut plane depth on the human tibia, the cut plane depth comprising a distance measured distally along the human tibia from the best fit plane; and generating a cutting jig for the arthroplasty procedure comprising a cut slot corresponding to the calculated cut plane.

20. The method of claim 19 further comprising determining a maximum depth of the depression feature of the table surface of the human tibia from the depression curve.

21. The method of claim 20 wherein the cut plane depth is greater than the maximum depth of the depression feature of the table surface of the human tibia as measured from the best fit plane for the plurality of points along the table surface of the human tibia.

22. A method for determining a cut plane through a human tibia for an arthroplasty procedure on a human knee, the method comprising:

receiving a plurality of two-dimensional (2D) images of a patient's joint subject to the arthroplasty procedure at a computing device;

determining a plane for a plurality of points along a table surface of a human tibia of a first set of 2D images of the plurality of 2D images, the table surface comprising at least a portion of a proximal end of the human tibia, said plurality of points comprising at least three points;

wherein the plane for the plurality of points along the table surface of the human tibia is a best fit plane along the table surface of the human tibia within the at least one of the plurality of 2D images;

calculating a cut plane for use during the arthroplasty procedure on a human knee;

wherein calculating the cut plane for use during the arthroplasty procedure comprises:

calculating a best fit plane normal vector to the best fit plane for the plurality of points along the table surface of the human tibia of the first set of 2D images of the plurality of 2D images; and orienting a normal vector of the cut plane to be parallel to the best fit plane normal vector;

wherein the cut plane is parallel to the calculated plane for the plurality of points along the table surface of the human tibia of the first set of 2D images of the plurality of 2D images; and generating a cutting jig for the arthroplasty procedure comprising a cut slot corresponding to the calculated cut plane.

23. A system for processing a medical scan of a patient in preparation for an arthroplasty procedure on a human knee, the system comprising:

a network interface configured to receive one or more medical images of a patient's anatomy; and a processing device in communication with the network interface; and a computer-readable medium in communication with the processing device configured to store information and instructions that, when executed by the processing device, performs the operations of:

receiving a plurality of two-dimensional (2D) images of a patient's joint subject to the arthroplasty procedure at a computing device;

determining a plane for a plurality of points along a table surface of a human tibia of a first set of 2D images of the plurality of 2D images, the table surface comprising at least a portion of a proximal end of the human tibia said plurality of points comprising at least three points;

wherein the plane for the plurality of points along the table surface of the human tibia is a best fit plane along the table surface of the human tibia within the at least one of the plurality of 2D images;

calculating a depression curve within at least one of the plurality of 2D images representing a depression feature of the table surface of the human tibia;

determining a cut plane depth on the human tibia, the cut plane depth comprising a distance measured distally along the tibia from the best fit plane;

calculating a cut plane for use during the arthroplasty procedure on a human knee, wherein the cut plane is parallel to the calculated plane for the plurality of points along the table surface of the human tibia of the first set of 2D images of the plurality of 2D images; and generating a cutting jig for the arthroplasty procedure comprising a cut slot corresponding to the calculated cut plane.

24. A system for processing a medical scan of a patient in preparation for an arthroplasty procedure on a human knee, the system comprising:

a network interface configured to receive one or more medical images of a patient's anatomy; and a processing device in communication with the network interface; and a computer-readable medium in communication with the processing device configured to store information and instructions that, when executed by the processing device, performs the operations of:

receiving a plurality of two-dimensional (2D) images of a patient's joint subject to the arthroplasty procedure at a computing device;

determining a plane for a plurality of points along a table surface of a human tibia of a first set of 2D images of the plurality of 2D images, the table surface comprising at least a portion of a proximal end of the human tibia said plurality of points comprising at least three points;

wherein the plane for the plurality of points along the table surface of the human tibia is a best fit plane along the table surface of the human tibia within the at least one of the plurality of 2D images;

calculating a best fit plane normal vector to the best fit plane for the plurality of points along the table surface of the human tibia of the first set of 2D images of the plurality of 2D images;

orienting a normal vector of the cut plane to be parallel to the best fit plane normal vector;

calculating a cut plane for use during the arthroplasty procedure on a human knee, wherein the cut plane is parallel to the calculated plane for the plurality of points along the table surface of the human tibia of the first set of 2D images of the plurality of 2D images; and generating a cutting jig for the arthroplasty procedure comprising a cut slot corresponding to the calculated cut plane.

* * * * *